(12) United States Patent
Aalders et al.

(10) Patent No.: US 10,814,052 B2
(45) Date of Patent: Oct. 27, 2020

(54) PUMP UNIT FOR A BREAST PUMP

(71) Applicant: KONINKLIJKE PHILIPS N.V., Eindhoven (NL)

(72) Inventors: Arnold Aalders, Eindhoven (NL); Ewout Van Der Laan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 324 days.

(21) Appl. No.: 15/561,715

(22) PCT Filed: Mar. 24, 2016

(86) PCT No.: PCT/EP2016/056479
§ 371 (c)(1),
(2) Date: Sep. 26, 2017

(87) PCT Pub. No.: WO2016/156173
PCT Pub. Date: Oct. 6, 2016

(65) Prior Publication Data
US 2018/0104395 A1    Apr. 19, 2018

(30) Foreign Application Priority Data

Apr. 1, 2015 (EP) .................................. 15162218

(51) Int. Cl.
*A61M 1/06* (2006.01)

(52) U.S. Cl.
CPC ........... *A61M 1/06* (2013.01); *A61M 2205/07* (2013.01); *A61M 2205/10* (2013.01);
(Continued)

(58) Field of Classification Search
CPC ...... A61M 1/00; A61M 1/06; A61M 2205/00; A61M 2205/07; A61M 2205/10; A61M 2205/3331; A61M 2205/3365; A61M 2205/42; A61M 2205/50; H02P 6/18; H02P 6/182; H02P 6/06; H02P 23/14; H02P 21/18; H02P 21/14; H02P 21/06;
(Continued)

(56) References Cited

U.S. PATENT DOCUMENTS 5,163,818 A  * 11/1992  Betsill ................... F04B 27/005
                                                        417/18
5,676,525 A  * 10/1997  Berner ................ A61M 1/0037
                                                        417/44.1
(Continued)

FOREIGN PATENT DOCUMENTS

JP     2013102867 A    5/2013
WO       0171190 A1   9/2001
(Continued)

*Primary Examiner* — Nathan R Price
*Assistant Examiner* — Mark A Igel

(57) ABSTRACT

The present invention relates to a pump unit for a breast pump for extracting milk from a human breast, comprising a motor for driving the pump unit, wherein the motor is configured to provide a motor feedback signal; a control unit for providing a control signal for controlling the motor; and an estimator for estimating a pressure provided by the pump unit based on the motor feedback signal and the control signal; wherein the control unit is configured to adjust the control signal based on the estimated pressure.

20 Claims, 4 Drawing Sheets

(52) U.S. Cl.
CPC .............. *A61M 2205/3331* (2013.01); *A61M 2205/3365* (2013.01); *A61M 2205/42* (2013.01); *A61M 2205/50* (2013.01)

(58) Field of Classification Search
CPC .... F04D 15/0066; F04B 49/065; F04B 49/08; F04B 49/20; F04B 2203/02; F04B 2203/0214; F04B 2205/04; F04B 2205/05
See application file for complete search history.

(56) References Cited

U.S. PATENT DOCUMENTS

| | | | | |
|---|---|---|---|---|
| 6,332,463 | B1 * | 12/2001 | Farrugia | G01F 1/50 |
| | | | | 128/204.18 |
| 8,052,635 | B1 * | 11/2011 | Kelly | A61M 1/0037 |
| | | | | 604/74 |
| 8,070,715 | B2 | 12/2011 | Quackenbush | |
| 8,070,716 | B2 * | 12/2011 | Sutrina | A61M 1/0031 |
| | | | | 604/73 |
| 8,137,305 | B2 * | 3/2012 | Kelly | A61M 1/0037 |
| | | | | 604/74 |
| 9,227,014 | B2 * | 1/2016 | Buckingham | A61M 5/1723 |
| 2002/0173695 | A1 * | 11/2002 | Skliar | A61M 1/10 |
| | | | | 600/16 |
| 2003/0130616 | A1 * | 7/2003 | Steil | A61B 5/4839 |
| | | | | 604/66 |
| 2004/0039243 | A1 * | 2/2004 | Bearnson | A61M 1/101 |
| | | | | 600/16 |
| 2008/0009815 | A1 * | 1/2008 | Grabenkort | A61M 1/0068 |
| | | | | 604/346 |
| 2008/0255503 | A1 * | 10/2008 | Quackenbush | A61M 1/064 |
| | | | | 604/74 |
| 2011/0054810 | A1 * | 3/2011 | Turner | A61M 1/0031 |
| | | | | 702/47 |
| 2013/0251540 | A1 * | 9/2013 | Paulus | F04D 15/0088 |
| | | | | 417/22 |

FOREIGN PATENT DOCUMENTS

| | | | | |
|---|---|---|---|---|
| WO | | 2014044472 A1 | 3/2014 | |
| WO | WO-2014037129 A1 * | | 3/2014 | ............. A61M 1/06 |

* cited by examiner

PUMP UNIT FOR A BREAST PUMP

FIELD OF THE INVENTION

The present invention relates to a pump unit for a breast pump for extracting milk from a human breast and a corresponding method and computer program.

BACKGROUND OF THE INVENTION

Breast pumps are well-known devices for extracting milk from a human breast. A breast pump may be used if a baby is not itself able to extract the milk or if the mother is separated from the baby, for example, if away from the baby at work. The use of a breast pump to extract milk can also be helpful to stimulate lactation in women with low milk supply.

Breast pumps can be manually operated, for example, by squeezing a handle or can also be electrically driven by a small electric motor. An electrically driven breast pump typically comprises one or two expression kits for application to the breast. The expression kits are connected to a pump unit via a tube system. The present invention relates to a breast pump with an electrically driven pump unit.

Breast pumps typically generate a cyclic vacuum at the breasts to express milk, wherein the vacuum profile advantageously mimics the sucking of a baby. Expressed milk is collected in a receptacle such as a baby feeding bottle. Mothers can set their preferred vacuum by adjusting one or more pump settings such as a vacuum level, profile and cyclic speed. Adjustment of the vacuum level is a matter of safety and quality. Firstly, the vacuum level must not become too deep to protect the mother. Secondly, the desired vacuum level should be applied in a reproducible manner.

The electric breast pump market can be split into two groups, single stroke and multiple stroke pumps. In the single stroke pumps, a large cylinder is generating the vacuum. The vacuum is typically controlled by adjusting the stroke of the large cylinder. A large stroke corresponds to a deep vacuum.

In multiple stroke pumps, a small and compact vacuum pump is used. The pump evacuates a small volume multiple times to reduce the pressure at the breast. The vacuum applied to the breast can be adjusted by adjusting pump settings such as a time interval during which the pump motor is active and by adjusting a speed of the pump motor. Retail breast pumps typically use low-cost brushed DC motors. The speed of the motor can be controlled by adjusting a supply voltage of the motor, most often through a pulse width modulation (PWM).

However, there are several limitations of such systems. The system does not take into account the individual anatomy of the woman using the device. Hence, depending on the size of breast and nipple, the volume to be evacuated and thus the vacuum level applied at the breast may be different even though the same pump settings such as time interval and supply voltage are applied. Some manufactures therefore use a pressure setting concept such as an adjustable dial, wherein no absolute value is set.

Moreover, in a hospital setting a woman may have to use different breast pumps. However, the same pump settings may result in a different vacuum level due to device spread between different breast pumps of the same type. One solution to overcome such device spread is extensive testing and calibration during the manufacturing process. However, individual testing and calibration of all devices leaving a manufacturing line is time consuming and costly.

Furthermore, a different vacuum level can occur even for the same breast pump applied by the same woman using the same settings in case of leakage.

A known solution to accurately set a desired vacuum level is to use a dedicated pressure sensor to determine and adjust the vacuum level provided by the pump unit. The pressure sensor has to be in fluid communication with a vacuum line of the expression kit.

For example, U.S. Pat. Nos. 8,052,635 and 8,137,305 disclose an electrical breast pump that continuously monitors a vacuum pressure applied to a milk collection system with a vacuum sensor attached to a vacuum line. A solid state pressure sensor or a piezoresistive pressure sensor can be used. Correspondingly, U.S. Pat. No. 8,070,715 discloses a breast pump with a pressure transducer for detecting an actual pressure. The pressure transducer is attached to a vacuum line.

However, disadvantages of using an additional pressure sensor attached to a vacuum line are added cost and complexity. A pressure sensor is an additional part that could potentially fail. This is particularly an issue in a hospital setting, where breast pumps require a long lifetime and robustness. Furthermore, the sensor has to be correctly attached to a vacuum line which can make the handling of the breast pump more inconvenient and can have a negative impact on system hygiene due to the additional sensor opening.

US 2011/0054810 A1 relates to an apparatus and method for determining a pressure in a topical negative pressure (TNP) system. Topical negative pressure therapy assists in the closure and healing of wounds. A flow meter is provided instead of a pressure sensor. A known relationship between the pump speed, pressure and a measured flow rate is used to calculate the pressure at the location where the flow meter is located.

WO 2014/044472 A1 discloses actuator control in a breast pump system with a power supply control module. A level of a pump motor current is used as an indicator of the vacuum pressure. If the motor current exceeds a predetermined threshold current value indicative of a pre-existing vacuum condition, a power supply control is arranged to reduce the speed of the pump motor.

U.S. Pat. No. 5,676,525 discloses a vacuum limiting medical pump. A current-limiting unit is provided to limit the created partial vacuum. An additional position detection device determines the suction volume of a pump cylinder unit.

WO 01/71190 A1 discloses an oscillating armature diaphragm pump. In order to measure a flow rate between two successive applications of a drive voltage to a coil during a time, during which no drive is effected, the voltage existing on the coil is detected and a flow rate measurement signal is generated therefrom.

SUMMARY OF THE INVENTION

Therefore, it is an object of the present invention to provide a pump unit for a breast pump which substantially alleviates or overcomes the above-mentioned problems. In particular, it is an object of the present invention to provide a pump unit for a breast pump to control a pressure provided by the pump unit accurately with high reliability over device lifetime and in a cost effective manner.

According to an aspect of the present invention, a pump unit for a breast pump for extracting milk from a human breast is provided, wherein the pump unit comprises:

a motor for driving the pump unit, wherein the motor is configured to provide a motor feedback signal;

a control unit for providing a control signal for controlling the motor; and an estimator for estimating a pressure provided by the pump unit based on the motor feedback signal and the control signal;

wherein the control unit is configured to adjust the control signal based on the estimated pressure.

In a further aspect of the present invention, a method for controlling a pressure generated by a pump unit for a breast pump for extracting milk from a human breast is presented, the method comprising the steps of:

providing a control signal for controlling a motor for driving the pump unit;

receiving a motor feedback signal of the motor for driving the pump unit;

estimating a pressure provided by the pump unit based on the motor feedback signal and the control signal; and adjusting the control signal based on the estimated pressure.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed pump unit and as defined in the dependent claims.

The present invention is based on the idea that a pressure to be generated by the pump unit can be seen as a load that has to be overcome by the pump unit. The pressure can be seen as a pneumatic load of the pump unit. Furthermore, a mechanical resistance to operate the pump unit, for example due to friction, can also be seen as a mechanical load that has to be overcome by the pump unit. Different loads will in turn have a different impact on the pump unit and in particular on the motor of the pump unit. In other words, driving a lower load requires less effort by the motor than driving a heavier load. The load substantially depends on the pressure in particular the negative pressure or vacuum that the motor of the pump unit has to work against. Hence, instead of using a pressure sensor attached to a vacuum line of the breast pump, it is suggested to indirectly estimate the pressure provided by the pump unit based on a motor feedback signal and a control signal for controlling the motor.

A "control signal" for controlling the motor as used herein can refer to a voltage and/or current applied to the motor, including but not limited to a pulse width modulation (PWM) control signal. A control signal can refer to a signal comprising information for controlling the motor which can be provided to power electronics that then power the motor dependent on the received control signal. In other words, a control signal for controlling the motor can refer to a signal indicative of a desired state or mode of operation of the motor for driving the pump unit.

A "motor feedback signal" as used herein can refer to a signal comprising information indicative of an actual state or mode of operation of the motor for driving the pump unit, which is influenced by the load driven by the motor.

Based on the motor feedback signal and the control signal, the estimator of the pump unit can estimate a pressure provided by the pump unit without using a separate pressure sensor. The estimation can comprise intermediate steps of estimating a load that is driven by the motor, determining a pneumatic load based thereon and matching the pneumatic load to a pressure value. Advantageously, the control unit and the estimator can be implemented in a microcontroller. Hence, control and estimation algorithms can be implemented at low cost.

Furthermore, the handling of the breast pump can be simplified since no separate pressure sensor has to be attached to a vacuum line of the breast pump. This also has a positive impact on hygiene because there is no additional sensor opening in the vacuum lines.

In other words, instead of actually measuring the pressure with a pressure sensor, a given control signal for controlling the motor is expected to result in a certain level of vacuum at the mother's breast. However, the accuracy of such an estimate is limited due to device spread and since a volume to be evacuated depends on the individual anatomy of the mother's breast. Device spread and the individual anatomy are unknown parameters. According to an aspect of the present invention, it is therefore suggested to further use feedback from the motor, wherein the motor feedback signal depends on the pressure provided by the pump unit, in order to more accurately estimate the pressure provided by the pump unit. The control unit can then adjust the control signal for controlling the motor based on the estimated pressure. The control unit can also adjust the control signal based on a desired pressure and the estimated pressure.

For example, the motor for driving the pump is driven by a control signal such as a given power, voltage or current and a feedback signal such as the motor speed is provided by the motor. Both, the measured speed as the feedback signal and the applied control signal are provided to the estimator. The pressure provided by the pump unit can be estimated by estimator based thereon. The details of a numerical model for estimation depend on the breast pump model, in particular on the pump and the expression kit. The estimated pressure can in turn be used to adjust the control signal for controlling the motor for driving the pump unit. Hence, for example in a hospital setting, the pump unit can adapt to different users.

According to an embodiment, the motor for driving the pump unit is a brushless motor, in particular a brushless DC motor (BLDC). A disadvantage of such brushless motors is that they are typically more expensive and require more complex control electronics than brushed DC motors, which are used in conventional breast pumps. However, the inventors have found that the use of brushless motors, in particular brushless DC motors provides a synergistic effect. For example, BLDCs can also be referred to as electronically commutated motors. A BLDC can comprise a rotor with a permanent magnet that is set into motion by an external rotating electromagnetic field. BLDCs can be powered by a control unit comprising an integrated inverter/switching power supply which produces an alternating current electric signal for generating the external field as a control signal to drive the motor. In order to determine an angular position of the motor and/or to apply the electric field substantially synchronized with a rotation of the rotor of the motor, the motor can provide a motor feedback signal to the control unit. Hence, BLDC motors typically have an inherent speed measurement used for electronic commutation.

The inventors have realized that such a motor feedback signal can be used in combination with the control signal to estimate a pressure provided by the pump unit. Hence, a synergistic effect is achieved in that the control signal and the motor feedback signal, which are already available in a brushless motor, are further used for estimating the pressure provided by the pump unit.

As an alternative to BLDCs, brushless AC (alternating current) synchronic motors can be used. In such motors the current drawn is a function of the torque generated, which could be used for control and, as a synergistic effect, also as a motor feedback for estimating the pressure provided by the pump unit of the breast pump.

In a refinement, said motor feedback signal is a motor feedback signal for electronic switching of the brushless motor and said estimation of the pressure provided by the pump unit is based on the motor feedback signal for electronic switching of the brushless motor. An advantage of this embodiment is, that a motor feedback signal which is normally provided by the motor to the control unit for regular operation of the brushless motor is also used for estimating the pressure provided by the pump unit. Hence, there is no need to use additional sensors. In particular there are no costs for a dedicated pressure sensor.

A further advantage of a brushless motor is a long lifetime and lower susceptibility to mechanical wear since the motor has no brushes that may wear. Hospital breast pumps typically require a long lifetime. A brushless motor typically requires less or sometimes even no maintenance.

In an embodiment, the motor further comprises a motor sensor for providing the motor feedback signal. Exemplary motor sensors are a speed sensor, an rpm sensor to determine the revolutions per minute, a tachometer, a Hall sensor, an angle sensor for determining a rotary angle of the rotor such as a rotary encoder. Optionally, the motor feedback signal can be obtained indirectly by determining a position of a movable part of the pump such as a piston, a membrane or an eccentric tappet. Furthermore, the motor feedback signal can be provided by evaluating a current/voltage/power, for example, by means of a spectral analysis to determine a rotary motor speed or by evaluating its transient behavior to determine an angular position.

In an embodiment, the motor feedback signal comprises at least one of a motor speed, a current, torque and an angular displacement of a rotor of the motor. It should be noted that the term angular displacement can refer to a position of the rotor in the motor and can also be used to determine the motor speed by evaluating an angular displacement over time.

In an embodiment, the estimator is configured to estimate an estimated motor parameter based on the control signal for controlling the motor; to determine an actual motor parameter based on the motor feedback signal; and to estimate the pressure provided by the pump unit based on a difference between the estimated motor parameter and the actual motor parameter. Advantageously, the estimated motor parameter is an estimated motor speed and the actual motor parameter is an actual motor speed. For example, when a given voltage is applied to the motor, the motor is expected to turn at a certain motor speed. However, depending on the load, the motor speed may be different. Based on this difference, a load that has to be driven by the motor can be derived and a pressure provided by the pump unit can be estimated based on this difference. Alternative parameters such as an angular position can be evaluated.

According to a further embodiment, the control unit is configured to obtain a desired pressure and to adjust the control signal based on a difference between the desired pressure and the estimated pressure. The desired pressure can be a value preset in the pump unit. Alternatively or in addition, an optional interface, in particular a user interface, is provided for setting a desired pressure to be provided by the pump unit. Instead of just having for example a dial to increase or decrease the pressure, i.e., for relative pressure changes, the pump unit according to an aspect of the present invention comprises an estimator for estimating a pressure provided by the pump unit. The estimated pressure can be used as feedback by the control unit for adjusting the control signal and thereby the actual pressure provided by the pump unit. In essence, decreasing or increasing the pressure via a dial or push bottoms can be seen as an open loop controller wherein a control variable is set by the user. The pump unit according to an aspect of the present invention, however, can be seen as a closed loop control system. The estimator provides an estimated pressure which can then be compared by with the desired pressure by the control unit. The control unit can then adjust an actual pressure provided by the pump unit based thereon.

In a further refinement of this embodiment, the control unit is configured to adjust the control signal to minimize the difference between the desired pressure and the estimated pressure. Hence, even though there is no pressure sensor provided in the pump unit, the pressure provided by the pump unit can be estimated by the estimator and used as a feedback signal for adjusting the pump unit such that the estimated pressure substantially corresponds to the desired pressure.

In an embodiment, the estimator comprises a model of at least parts of the breast pump. The estimator receives the motor feedback signal and the control signal for controlling the motor as input signals and, based on the model of at least parts of the breast pump, the estimator determines an estimate of a pressure provided by the pump unit. The model can comprise characteristics of the pump, a fluid model, a stroke volume, a volume to be evacuated and so on and in particular a model of a used expression kit. Since the pump unit does not comprise a pressure sensor, the pressure provided by the pump unit cannot be determined by direct observation. However, as described above, the pressure can be seen as a state that influences the motor feedback signal provided by the motor. Knowing a relation between the motor feedback signal and the physical state pressure, the estimator can estimate the pressure provided by the pump unit.

According to a further embodiment, the estimator comprises a Kalman filter, in particular an extended and/or unscented Kalman filter. It was found that a relation between the pressure provided by the pump unit and the motor feedback signal can suffer from heavy nonlinear dynamics. Therefore, it is advantageous to use an unscented Kalman filter which is able to deal with heavy nonlinear dynamics. An alternative filter, which is able to deal with nonlinearities can also be used.

According to a further embodiment, the estimator is configured to initialize the estimated pressure at startup as ambient pressure. Startup in this context can refer to the first revolutions of the pump motor. During such an initial phase, the load that is seen by the pump motor is not determined by a pneumatic resistance caused by the vacuum but rather by a mechanical load, for example due to friction of a piston when using a piston pump. Due to manufacturing spread, different devices of one model can exhibit different initial mechanical loads. By determining this initial mechanical load upon startup, the pump can be calibrated for ambient pressure. A subsequent increase in the load can then be attributed to a vacuum that builds up in the breast pump.

Hence, the contributions of mechanical load and pneumatic load due to the vacuum can be separated such that the pressure provided by the pump unit can be estimated in a reliable manner.

According to an embodiment, the control unit is configured to limit a motor speed of the motor based on the motor feedback signal and/or on the estimated pressure. As explained above, the motor speed depends on the load that has to be overcome by the pump unit. Hence, the motor speed changes with the vacuum level. At the start of an expression session, a mother may switch on the system and only then place ii on the breast. In such a non-breast situation the load can be very low and can therefore lead to high motor speeds. A high motor speed leads to a high pump throughput and has the advantage that the expression kit can be quickly evacuated. However, a high motor speed may generate an unpleasant sound or noise. An audible frequency can correspond to a motor speed or frequency in revolutions per second [Hz], It is therefore suggested to limit the motor speed to provide a more desirable sound profile. Furthermore, when the breast pump is placed on the breast, the pump unit quickly evacuates the expression kit. The vacuum and thus also the load at the pump unit increases. Since the motor speed depends on the load, the sound or noise of the pump unit changes rapidly. By limiting the motor speed, a more desirable sound profile can be generated when placing the expression kit at the breast.

Moreover, an increase of the motor speed, i.e. an acceleration of the motor speed, can also be limited. This can further prevent a sudden noise increase, which would also be unpleasant.

According to a further embodiment, the control unit is configured to determine a state, wherein the breast pump is not attached to the human breast based on the estimated pressure. This can also be referred as a non-breast situation. For example, the motor speed can be further reduced in this state and will then switch or change to regular operation, when the breast pump is attached to the human breast. Attachment to the breast can be determined by observing the estimated pressure and determining when the estimated pressure changes, in particular, when the estimated pressure drops below a predetermined threshold compared to ambient pressure.

BRIEF DESCRIPTION OF THE DRAWINGS

These and other aspects of the invention will be apparent from and elucidated with reference to the embodiments described hereinafter. In the following drawings

DETAILED DESCRIPTION OF THE EMBODIMENTS

Figure 1:
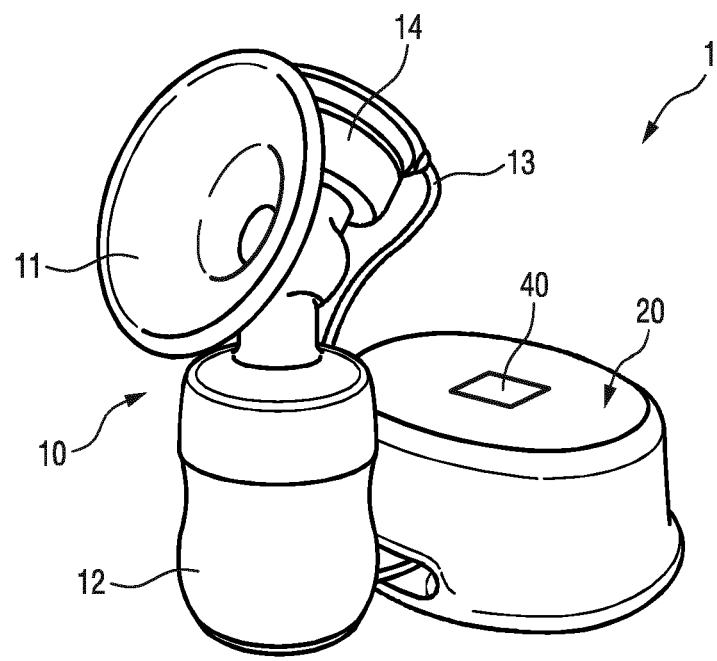
FIG. 1 shows a perspective view of a first embodiment of a breast pump.

FIG. 1 shows an embodiment of a breast pump. The breast pump is therein denoted in its entirety with reference numeral 1.

The breast pump 1 comprises an expression kit 10 and a pump unit 20. The expression kit 10 comprises a breast receiving funnel 11 and a receptacle 12 in form of a baby feeding bottle. The pump unit 20 comprises a vacuum pump 21 with a motor 22 for driving the pump unit and a control unit 23 for providing a control signal for controlling the motor 22 of the vacuum pump 21 (schematically shown in FIG. 3). The vacuum pump 21 of the pump unit 20 is connected to the expression kit 10 via a tube 13. The pump unit 20 may thus be arranged locally remote from the expression kit 10, for example on a desktop or at any other suitable position. However, this is not intended to be limiting. The pump unit 20 comprising the vacuum pump 21 and the control unit 23 could also be arranged at the expression kit 10. The tube 13 is connected to a vacuum chamber 14 that is comprised in the housing of the expression kit 10. The vacuum chamber 14 has the function to impart the vacuum generated by the vacuum pump 21 of the pump unit 20 to the breast receiving funnel 11. The breast pump 1 can comprise a user interface 40 for setting a desired vacuum level, profile and/or cycle. Advantageously, the pump unit 20 generates a cyclic vacuum at the breast, wherein the vacuum profile preferably mimics the sucking of a baby.

Figure 2:
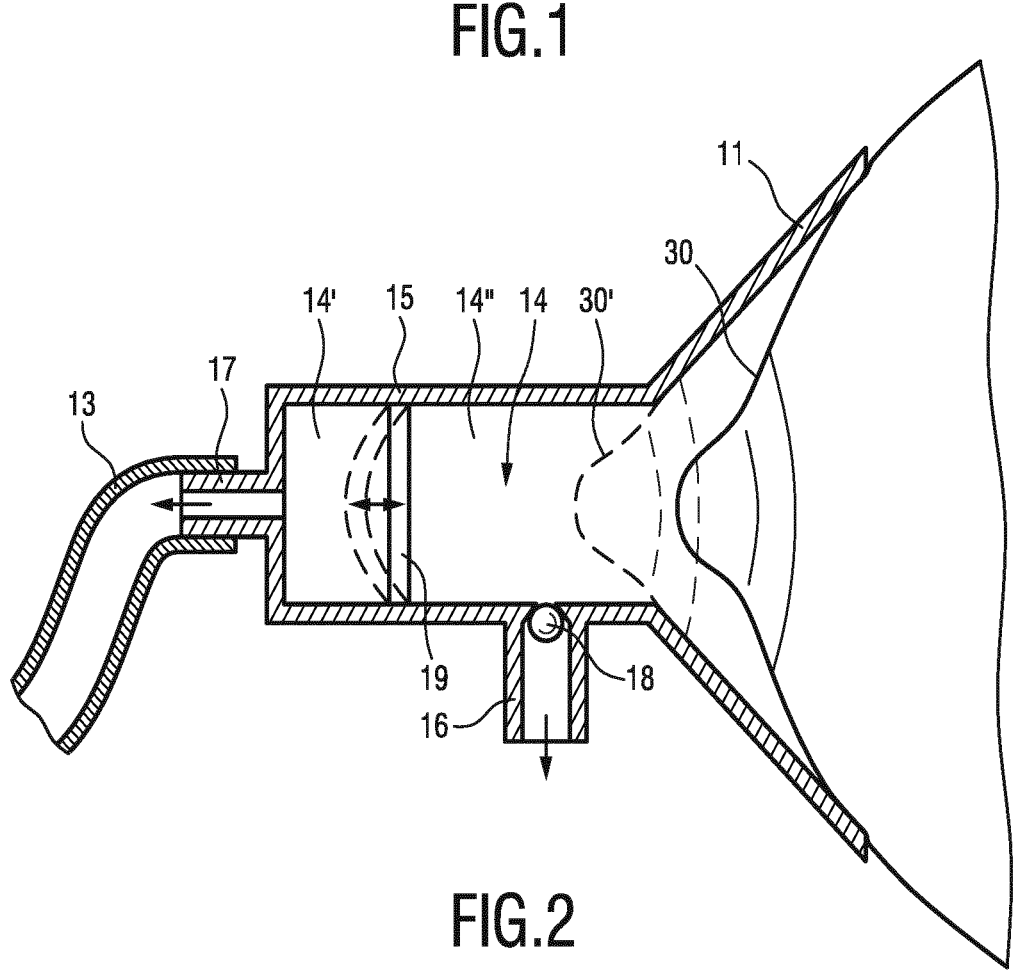
FIG. 2 shows a cross section of a top portion of an expression kit according to a further embodiment.

FIG. 2 shows a cross section of a top portion 15 of an expression kit 10 according to a further embodiment in more detail. The top portion 15 of the expression kit comprises a breast receiving funnel 11, a vacuum chamber 14, a milk outlet 16 and a connector 17 for connection to a vacuum tube 13.

The top portion 15 of the expression kit can be attached to the breast 30 of a woman by means of the breast receiving funnel 11. A center of the breast receiving funnel is arranged over a nipple of the breast 30. During milk extraction, the pump unit 20 generates an underpressure or vacuum in the vacuum chamber 14. Thereby, milk is expressed from the breast 30. The expressed milk can leave the top portion 15 of the expression kit 10 through the milk outlet 16 towards a receptacle 12.

A volume of the vacuum chamber 14, which is to be evacuated during each cycle, substantially depends on a size and shape of breast 30 and nipple. Such differences are indicated in FIG. 2 by different breasts 30 and 30'. A larger volume has to be evacuated for breast 30 and a smaller volume has to be evacuated for breast 30'. Hence, if the same pump settings, such as a time interval during which the pump motor 22 of the pump unit 20 is active and speed of the pump motor 22, are applied, a different vacuum level will be reached. A smaller volume is evacuated more quickly and a deeper vacuum level is reached for the same pump settings.

Besides controllability in a single product, a manufacturer of breast pumps is interested in a spread of performance between different products. A conventional open loop control does not allow a system to compensate for spread in vacuum performance of different breast pumps of the same type. For retail, product spread is less critical because a mother is likely to use only her own breast pump, so comparing to other breast pumps of the same type is not a big issue. However, hospital breast pumps are typically used by different mothers and one mother could potentially use different breast pumps of the same type. Ensuring that one setting on the pump results in identical vacuum performance and thus same milk extraction and user experience is a huge benefit for the user.

Figure 3:
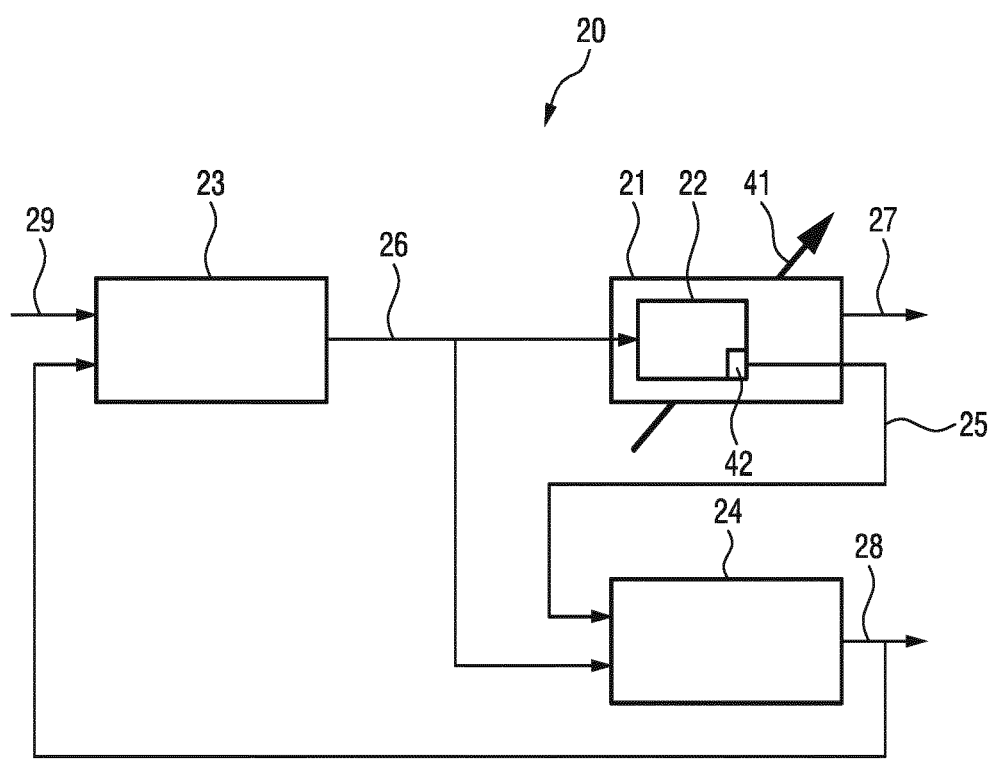
FIG. 3 shows an exemplary block diagram of a pump unit according to an embodiment.

FIG. 3 shows an embodiment of a pump unit 20 according to an aspect of the present invention. The pump unit 20 comprises a vacuum pump 21 with a motor 22, a control unit 23 and an estimator 24.

The motor 22 is configured to provide a motor feedback signal 25. The control unit 23 is configured to provide a control signal 26 for controlling the motor 22. By controlling the motor 22, the control signal 26 influences an actual pressure 27 provided by the pump unit 20. The estimator 24 is configured to estimate the pressure 28 provided by the pump unit 20 based on the motor feedback signal 25 and the control signal 26. Hence, the estimator 24 provides an estimated pressure 28 and not a measured actual pressure 27. The control unit 23 is further configured to adjust the control signal 26 based on the estimated pressure 28. Hence, even though the actual pressure 27 is not directly measured by a pressure sensor, feedback can be provided to the control unit 23 by means of the estimated pressure 28 derived from the motor feedback signal 25 and the control signal 26. Optionally, a desired pressure 29 can be provided as an input to the control unit 23. A desired pressure 29 can be a desired pressure level, profile and/or cycle which can be set by the user via the user interface 40, as shown in FIG. 1.

The underlying concept according to an aspect of the present invention will be described in more detail with reference to FIGS. 4A to 4C.

Figure 4A:
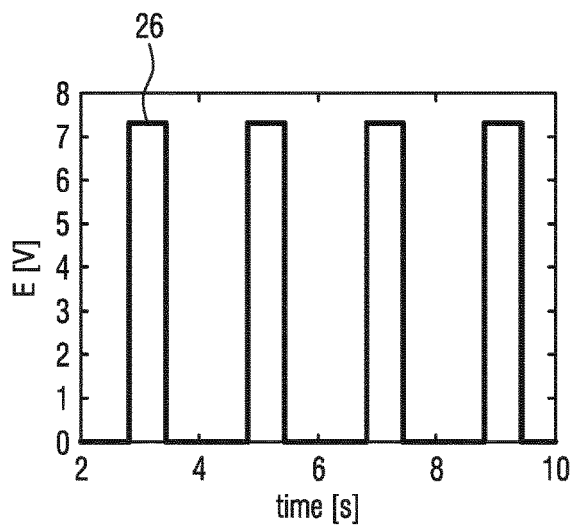
FIG. 4A shows an exemplary graph of a control signal for controlling a motor for driving a pump unit.

FIG. 4A shows an exemplary graph of a control signal 26 provided by the control unit 23. The horizontal axis denotes the time t in seconds, whereas the vertical axis denotes a supply voltage E in volts. In this non-limiting embodiment the control signal 26 is a supply voltage to power the motor 22 for driving the pump unit 20 that is switched on and off in a periodic manner. Of course, different profiles or curves of the control signal 26 could be used to create a desired vacuum profile.

Figure 4B:
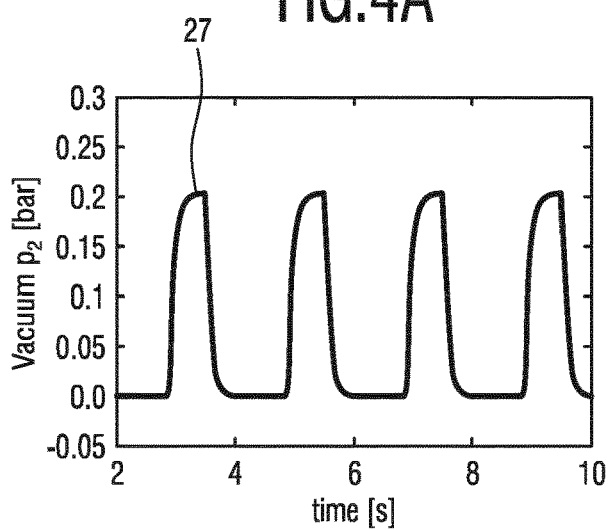
FIG. 4B shows an exemplary graph of a pressure provided by the pump unit.

FIG. 4B shows an exemplary graph of the actual pressure 27 provided by the pump unit 20 in response to the control signal 26 as shown in FIG. 4A. The horizontal axis again denotes the time t in seconds, whereas the vertical axis denotes a vacuum pressure p in bar. Breast pumps according to the prior art, as mentioned above regarding the background of the present invention, use a dedicated pressure sensor or pressure transducer to directly measure the actual pressure 27.

However, the pump unit 20 according to an aspect of the present invention follows a substantially different approach. The inventors have realized that the actual pressure 27 can be seen as a load that has to be overcome by the vacuum pump 21 of the pump unit 20. Hence, the actual pressure 27 can be seen as a pneumatic load of the pump unit 20, which in turn has an impact on the motor 22 of the pump unit 20. The variable pneumatic load of the vacuum pump 21 is indicated by an arrow 41 in FIG. 3. Instead of directly measuring the actual pressure 27, firstly the motor 22 is configured to provide a feedback signal 25 and secondly an estimator 24 is provided for estimating the pressure 28 provided by the pump unit 20 based on the feedback signal 25 and the control signal 26 applied to the motor 22.

Figure 4C:
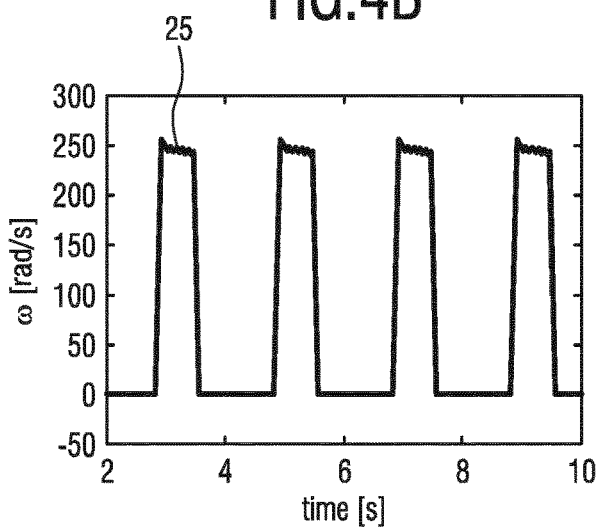
FIG. 4C shows an exemplary graph of a motor speed.

FIG. 4C shows an exemplary graph of a motor speed as an exemplary feedback signal 25 provided by the motor 22 in response to the control signal 26 as shown in FIG. 4A and the actual pressure 27 as shown in FIG. 4B. The horizontal axis in FIG. 4C again denotes the time t in seconds, whereas the vertical axis denotes the motor speed $\omega$ in radians per second. As can be seen from FIG. 4C, the motor 22 exhibits a load-dependent motor speed $\omega$. When the control signal 26 in FIG. 4A is applied, the motor speed $\omega$ in FIG. 4C increases rapidly. A given control signal 26 for controlling the motor is expected to result in a certain motor speed $\omega$.

However, as the vacuum 27 in FIG. 4B builds up, the motor speed $\omega$ in FIG. 4C reduces again. The estimator 24 is thus configured to estimate the pressure 28 provided by the pump unit 20 based on said motor feedback signal 25 and the control signal 26. The motor feedback signal 25 and the control signal 26 are fed to the estimator 24, which contains a numerical model of a relationship between control signal 26, motor feedback signal 25 and a resulting estimated pressure 28. It should be noted that the particular details of the numerical model depend on the implementation of the system, such as the characteristics of motor 22, vacuum pump 21, expression kit 10 and the like. The skilled person will appreciate that changes in the physical system lead to changes in the numerical estimation model. The shown example is to be understood as a non-limiting embodiment. The estimated pressure 28 is in turn used by the control unit 23 to adjust the control signal 26 provided to the motor 22. A closed control loop can thus be realized without measuring the actual pressure 27 provided by the pump unit 20.

Referring again to FIG. 3, the motor 22 can be a brushless DC motor (BLDC). The use of a BLDC has the advantage that BLDCs often already have an inherent motor speed measurement used for electronic commutation. This motor speed measurement is often readily available as a sensor signal. In addition BLDCs have no brushes that may lead to time-variant friction torque, so speed-torque characteristics are well defined. These two properties make a BLDC well-suited to estimate an applied motor torque, as an indicator of the load that has to be overcome by the vacuum pump 21, and thus the estimated pressure 28 in the system.

Alternatively or in addition, the pump unit 21 can comprise a motor sensor 42 such as speed sensor for providing the motor speed $\omega$ as the motor feedback signal 25 to the estimator 24.

The control unit 23 and the estimator 24 can advantageously be implemented by means of a microcontroller.

Due to device spread, a mechanical load to drive the pump unit 20 can be different for different pump units 20 of the same type. The mechanical load can also change over device lifetime, for example because of wear. In an embodiment, the control unit 23 is thus configured to determine an initial mechanical load based on the control signal 26 and the motor feedback signal 25 upon startup. Hence, the load at ambient pressure can be determined for calibration of the pump unit 20. For example, referring to FIGS. 4A to 4C, the initial motor speed $\omega$ right after onset of a voltage of the control signal 26 can be used for calibration.

Referring to FIG. 3, the control unit 23 can be further configured to limit a motor speed of the motor based on the motor feedback signal and/or the estimated pressure. Hence, a more pleasant sound profile can be generated as explained above.

Furthermore, the control unit 23 can be configured to reduce a motor speed in a non-breast situation, as explained above.

In view of safety considerations, the maximum vacuum level that can be set should be limited. Since the vacuum level substantially depends on the size of breast and nipple, conventional pump units without feedback are designed not to exceed such a safety limit in a worst case scenario, i.e., for a small volume to be evacuated. Hence, a range of pump settings that can be set by the user is artificially limited. However, assuming that the individual anatomy of a woman provides a larger volume to be evacuated, the maximum vacuum level that can be reached can be substantially lower than the safety limit. In consequence, a vacuum level that may be best for extraction might not even be reached. With the pump unit 20 according to an aspect of the present invention, the pressure provided by the pump unit can be estimated based on a motor feedback signal and a control signal. The control unit 23 can therefore be configured to adjust the control signal for controlling the pump motor 22 based on the estimated pressure such that the estimated pressure does not exceed a predetermined safety limit. Hence, by using the estimated pressure as the feedback, a broader range of pump settings can be used. It should be noted that even a rough estimate of a pressure provided by the pump unit can improve an expression efficiency in this situation.

Referring again to FIG. 2, the milk outlet 16 can optionally comprise a valve 18, in particular a check valve or one-way valve such that expressed milk can leave the vacuum chamber 14 but prevents reflux from the receptacle 12 towards the vacuum chamber 14. During milk extraction, a one-way valve can open and close automatically in accordance with a time-variable underpressure generated by the pump unit 20, as e.g. shown in FIG. 4B. At the beginning of the underpressure cycle, an underpressure will be created in the vacuum chamber 14 which causes the one-way valve to close and to extract the milk from the breast 30. If the pressure then returns back e.g. to atmospheric pressure during said cycle, the one-way valve opens up and the milk flows into the milk receptacle 12 by gravity.

Optionally, the vacuum chamber 14 is separated by means of a hygienic shield 19 into a first portion 14' and a second portion 14" of the vacuum chamber as shown in FIG. 2. The first portion 14' is directly connected to the pump unit 20 by means of the connector 17 and tube 13. The second portion 14" is directly connected to the breast receiving funnel 11 and the milk outlet 16. The hygienic shield 19 can, for example, be a breathable membrane that is gas-permeable and liquid-impermeable. Alternatively, the hygienic shield 19 can be a non-permeable, resilient diaphragm. A movement of such a resilient diaphragm is exemplarily shown in FIG. 2 and indicted by an arrow. Since the hygienic shield 19 is gas-permeable or movable, a vacuum applied to the first portion 14' of the vacuum chamber also causes a vacuum in the second portion 14" for expressing milk from the human breast 30. The hygienic shield 19 prevents milk from entering the vacuum line 13 and/or pump unit 20.

Figure 5:
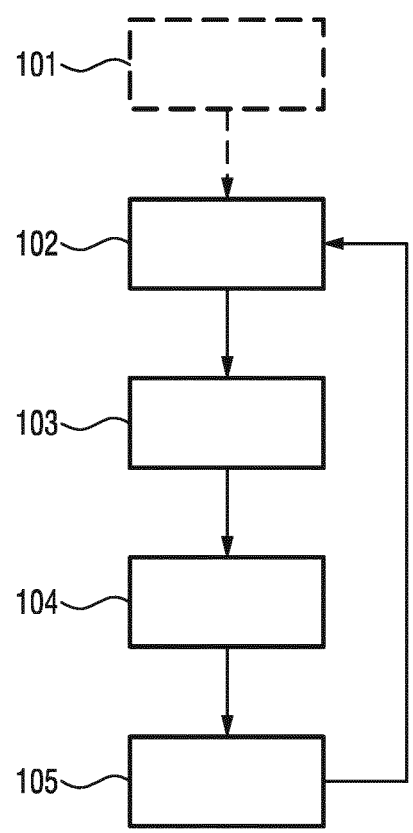
FIG. 5 shows a flow chart of a method according to an embodiment.

FIG. 5 summarizes the method for controlling a pressure 27 generated by a pump unit 20 for a breast pump 1 for extracting milk from a human breast 30. In a first optional step 101 the mother selects a desired pressure via a user interface 40 of the breast pump 1. In a second step 102 the control unit 23 provides a control signal 26 for controlling the motor 22 for driving the pump unit 20. In a third step 103 a motor feedback signal 25 of the motor 22 for driving the pump unit 20 is received. In a fourth step 104 the pressure 28 provided by the pump unit 20 is estimated based on the motor feedback signal 25 and the control signal 26. In step 105 the control signal 26 is adjusted based on the estimated pressure 28. Hence, a closed control loop is provided for controlling the motor 22 and thus the actual pressure 27 provided by the pump unit 20 based on the estimated pressure 28. In particular the actual pressure 27 can be controlled to correspond to the desired pressure 29 of the mother. It should be noted that steps such as steps 102 and 103 can also be performed in a different sequence or also be performed in parallel, as appropriate.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A pump unit for a breast pump for extracting milk from a human breast, the pump unit comprising:
    a motor for driving the pump unit, wherein the motor is configured to provide a motor feedback signal;
    a control unit for providing a control signal for controlling the motor; and
    an estimator for estimating a pressure provided by the pump unit based on the motor feedback signal and the control signal;
    wherein the control unit is configured to obtain a desired pressure and to adjust the control signal based on a difference between the desired pressure and the estimated pressure.

2. The pump unit according to claim 1, wherein the motor is a brushless motor.

3. The pump unit according to claim 2,
    wherein the motor feedback signal provides the motor feedback signal for an electronic switching of the brushless motor; and
    wherein the estimation of the pressure provided by the pump unit is based on the motor feedback signal for the electronic switching of the brushless motor.

4. The pump unit according to claim 1, wherein the motor further includes a motor sensor for providing the motor feedback signal.

5. The pump unit according to claim 1, wherein the motor feedback signal includes at least one of a motor speed, a current, a torque and an angular displacement of a rotor of the motor.

6. The pump unit according to claim 1, wherein the estimator is configured to estimate an estimated motor parameter based on the control signal for controlling the motor, to determine an actual motor parameter based on the motor feedback signal, and to estimate the pressure provided by the pump unit based on a difference between the estimated motor parameter and the actual motor parameter.

7. The pump unit according to claim 6,
    wherein the estimated motor parameter is an estimated motor speed; and
    wherein the actual motor parameter is an actual motor speed.

8. The pump unit according to claim 1, wherein the control unit is configured to adjust the control signal to minimize the difference between the desired pressure and the estimated pressure.

9. The pump unit according to claim 1, wherein the estimator includes a model of at least parts of the breast pump.

10. The pump unit according to claim 1, wherein the estimator includes a Kalman filter.

11. The pump unit according to claim 1, wherein the estimator is configured to initialize the estimated pressure at startup as ambient pressure.

12. The pump unit according to claim 1, wherein the control unit is further configured to limit a motor speed of the motor based on at least one of the motor feedback signal and on the estimated pressure.

13. The pump unit according to claim 1, wherein a speed of the motor for driving the pump is load-dependent.

14. The pump unit according to claim 13, wherein the control unit is configured to determine an initial mechanical load to drive the pump unit based on the control signal and the motor feedback signal at startup.

15. The pump unit according to claim 1, wherein the control unit is configured to apply the control signal in a periodic manner.

16. The pump unit according to claim 15, wherein a speed of the motor sequentially increases, peaks and decreases during an application of the control signal by the control unit to the motor.

17. The pump unit according to claim 1,
wherein the control signal is a supply voltage; and
wherein the control unit is configured to apply the supply voltage to the motor in a periodic manner.

18. The pump unit according to claim 17, wherein a speed of the motor sequentially increases, peaks and decreases during an application of the supply voltage by the control unit to the motor.

19. A method for controlling a pressure generated by a pump unit for a breast pump for extracting milk from a human breast, the method comprising the steps of:
providing, by a control unit of the pump unit, a control signal for controlling a motor of the pump unit for driving the pump unit;
providing, by the motor, a motor feedback signal based on the motor driving the pump unit;
estimating, by an estimator of the pump unit, a pressure provided by the pump unit to the breast pump based on the motor feedback signal and the control signal;
configuring the control unit to obtain a desired pressure; and
adjusting, by the control unit, the control signal based on a difference between the desired pressure and the estimated pressure.

20. Computer program comprising non-transitory program code means for causing a computer to carry out the steps of the method as claimed in claim 19 when the computer program is carried out on the computer.

* * * * *